United States Patent
Swensson et al.

(10) Patent No.: US 6,443,591 B1
(45) Date of Patent: Sep. 3, 2002

(54) CANOPY ASSEMBLY

(75) Inventors: Earl S. Swensson, Franklin; David S. Gilbert, Mt. Juliet, both of TN (US)

(73) Assignee: Wellness, LLC, Nashville, TN (US)

( * ) Notice: Subject to any disclaimer, the term of this patent is extended or adjusted under 35 U.S.C. 154(b) by 0 days.

(21) Appl. No.: 09/353,435

(22) Filed: Jul. 15, 1999

(51) Int. Cl.⁷ .................................................. F21S 1/02
(52) U.S. Cl. ....................... 362/147; 362/234; 362/240; 362/130; 362/801
(58) Field of Search .......................... 362/33, 147, 149, 362/225, 234, 240, 801, 804, 253, 130

(56) References Cited

U.S. PATENT DOCUMENTS

| | | | |
|---|---|---|---|
| 3,097,287 A | * 7/1963 | Knoll et al. | ................. 362/149 |
| 3,701,895 A | 10/1972 | Sweetser | |
| 4,403,275 A | 9/1983 | Oser | |
| 4,680,684 A | * 7/1987 | Wolber | ......................... 362/130 |
| 4,681,024 A | * 7/1987 | Ivey | ............................. 362/149 |
| 4,734,835 A | 3/1988 | Vines et al. | |
| 4,905,433 A | * 3/1990 | Miller | ......................... 362/130 |
| 4,910,650 A | 3/1990 | Goralnik | |
| 5,038,254 A | 8/1991 | Fabbri et al. | |
| 5,086,375 A | 2/1992 | Fabbri et al. | |
| 5,188,449 A | * 2/1993 | Davis et al. | ................. 362/225 |
| 5,613,757 A | 3/1997 | Polk | |
| 5,664,864 A | 9/1997 | Kuth | |
| 5,772,314 A | 6/1998 | Brumer | |
| 5,820,247 A | * 10/1998 | Schuler | ....................... 362/149 |
| 5,934,783 A | * 8/1999 | Yoshikawa | ................... 362/149 |

FOREIGN PATENT DOCUMENTS

DE 1076057 * 4/1957 ................... 362/33

* cited by examiner

Primary Examiner—Sandra O'Shea
Assistant Examiner—Peggy A Neils
(74) Attorney, Agent, or Firm—Waddey & Patterson; Lucien Wayne Beavers

(57) ABSTRACT

A canopy assembly is provided for use over a hospital bed in a health care environment. The canopy assembly includes an elongated housing which is preferably a unitary molded plastic shell. The housing has a straight first end for abutting a wall adjacent a head of the bed and has a rounded second end over the foot of the bed. The housing has a rectangular shaped interior opening disposed therein within which is received a rectangular shaped light box having a backlit translucent scenic panel thereon. The housing includes a semi-circular shaped opening within which is received an air diffuser which is connected to an HVAC system in the ceiling of the room. The housing includes a horseshoe shaped interior panel having a plurality of circular openings defined therein within which are received a plurality of task lights.

24 Claims, 4 Drawing Sheets

CANOPY ASSEMBLY

BACKGROUND OF THE INVENTION

1. Field of the Invention

The present invention relates generally to lighting apparatus, and more particularly, but not by way of limitation, to a lighting apparatus designed for use in a modular hospital room.

2. Description of the Prior Art

There is a need in a hospital room or other health care environment for effective lighting in the area of the patient's bed. For example, U.S. Pat. No. 5,038,254 to Fabbri, et al. and U.S. Pat. No. 5,086,375 to Fabbri, et al., both are directed to medical light systems designed to be installed in the ceiling above a patient's bed. These systems include reading lights, examination lights and ambient lights. Fabbri et al. does not, however, deal with providing air conditioning or ventilation, nor does it deal with providing an aesthetically pleasing environment for the patient.

There is, therefore, a need in the art for improved illumination systems which provide in a modular and aesthetically pleasing form all of the necessary illumination, and also a diffuser outlet for ventilation system.

SUMMARY OF THE INVENTION

The present invention provides a canopy assembly for mounting on a ceiling over a bed. The assembly includes an elongated housing having a straight first end abutting a wall adjacent a head of the bed, and having a rounded second end. The housing includes a horseshoe shaped interior panel having a plurality of light receiving openings defined therein. A plurality of light fixtures are received in the light receiving openings of the horseshoe shaped interior panel. The housing also includes a rectangular shaped interior opening within which a rectangular light box is disposed. The light box utilizes fluorescent back-lighting and has a translucent panel preferably carrying a soothing and pleasant outdoor scene or the like. The housing further includes a semi-circular shaped interior opening within which is received an air diffuser.

The assembly may also include other openings for ambient lights and reading lights.

The housing preferably is an integrally molded plastic structure which is supported from a framework which is in turn suspended from the ceiling, so that the entire housing with most or all lights and the diffuser panel may be installed in a single action.

It is therefore, an object of the present invention to provide improved lighting systems and ambience for hospital rooms.

Another object of the present invention is to provide improved outlets for heating, ventilating and air conditioning systems for hospital rooms.

Still another object of the present invention is the provision of a modular unit providing both lighting and ventilation above a bed.

Another object of the present invention is the provision of a combination lighting and ventilating module.

Still another object of the present invention is the provision of a lighting system which provides a pleasant soothing ambiance for the patient.

Other and further objects, features and advantages of the present invention will be readily apparent to those skilled in the art upon a reading of the following disclose when taken in conjunction with the accompanying drawings.

DETAILED DESCRIPTION OF THE PREFERRED EMBODIMENTS

Figure 1:
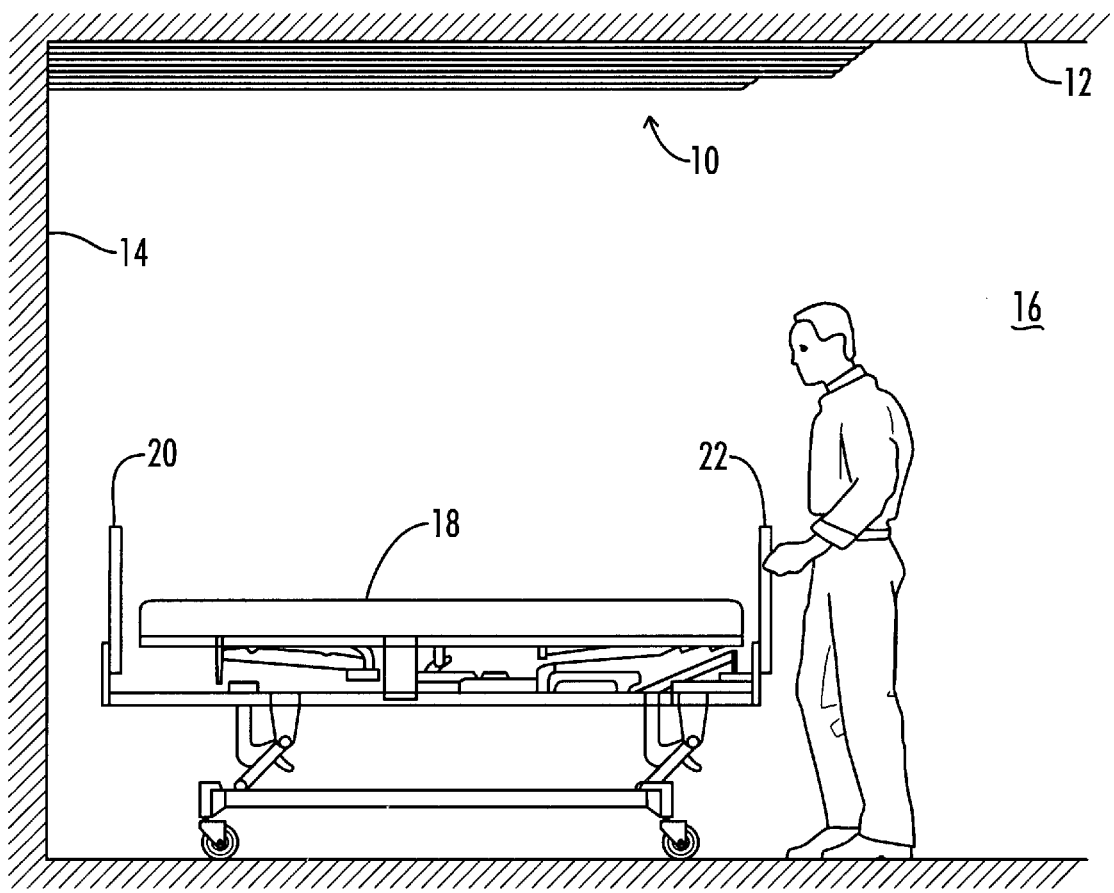
FIG. 1 is a schematic illustration of a patient bed in a hospital room with the illumination and ventilation apparatus of the present invention in place on the ceiling above the bed.

Referring now to the drawings, and particularly to FIG. 1, the canopy assembly of the present invention is shown and generally designated by the numeral 10. In FIG. 1, the canopy assembly 10 is shown mounted on a ceiling 12 and abutting a wall 14 of a room 16. A hospital bed 18 having a head 20 and foot 22 is shown in place below the canopy assembly 10.

Figure 2:
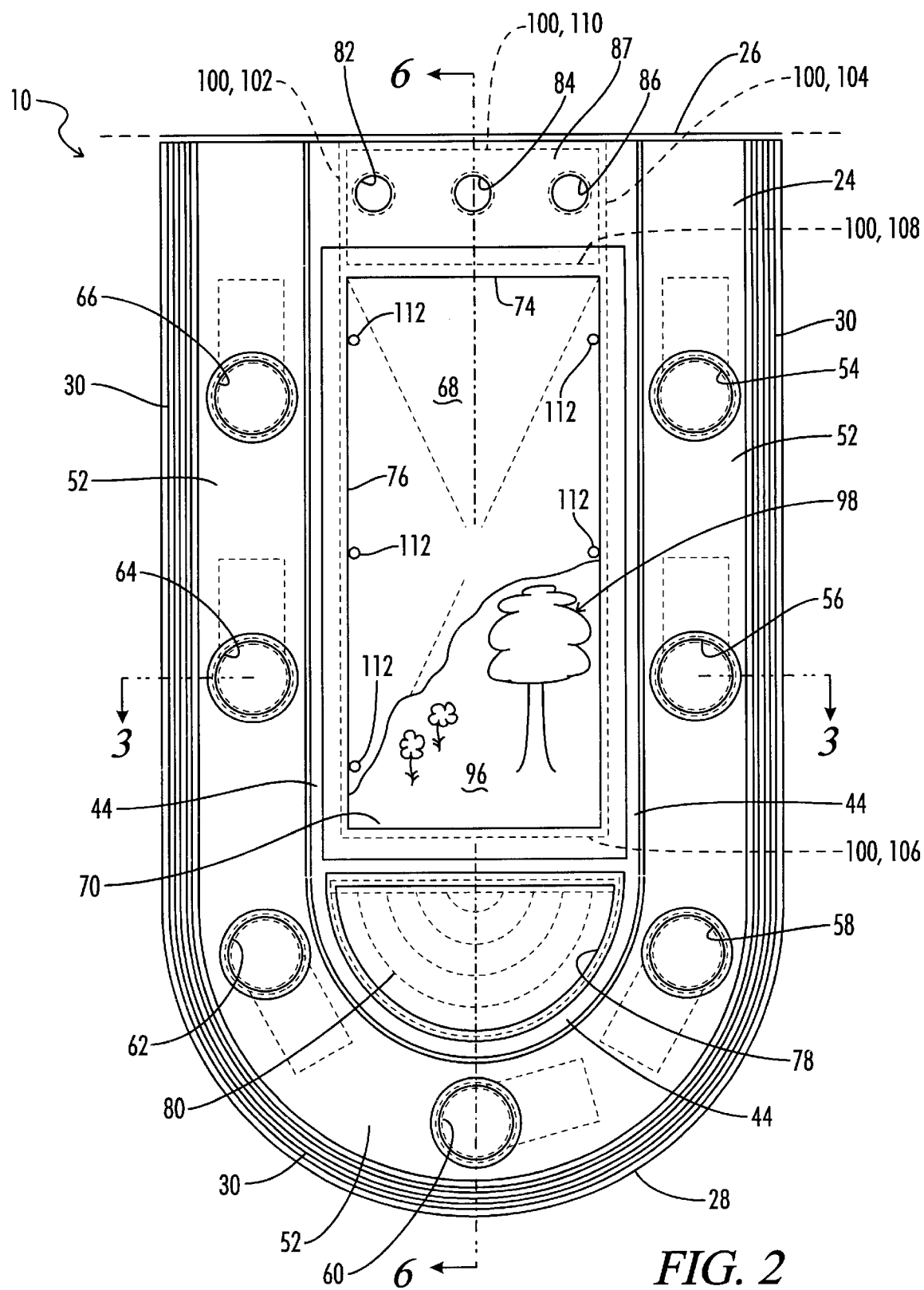
FIG. 2 is a bottom view of the canopy assembly of the present invention.

Referring now to FIG. 2, a bottom view is shown of the canopy assembly 10. The canopy assembly 10 includes an elongated housing 24 having a straight first end 26 which abuts the wall 14 adjacent the head 20 of the bed 18, and has a rounded second end 28.

The housing 24 is preferably a single integrally molded plastic shell having a plurality of openings defined therein for receiving the various lighting fixtures and an air diffuser for an air conditioning system.

Figure 3:
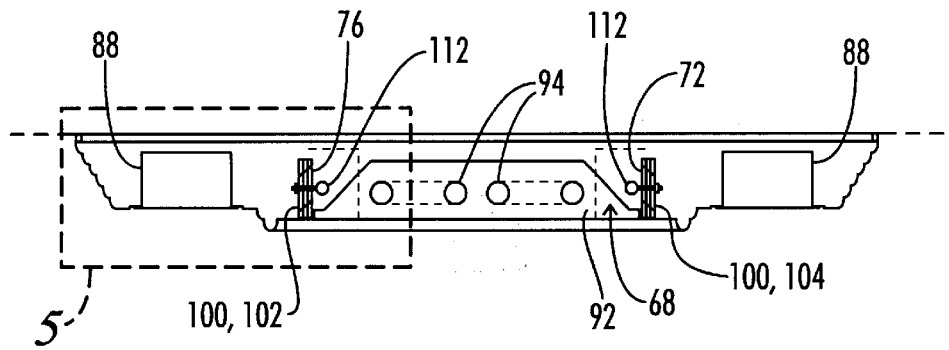
FIG. 3 is a section view of the canopy assembly of FIG. 2 taken along line 3—3 of FIG. 2.
Figure 5:
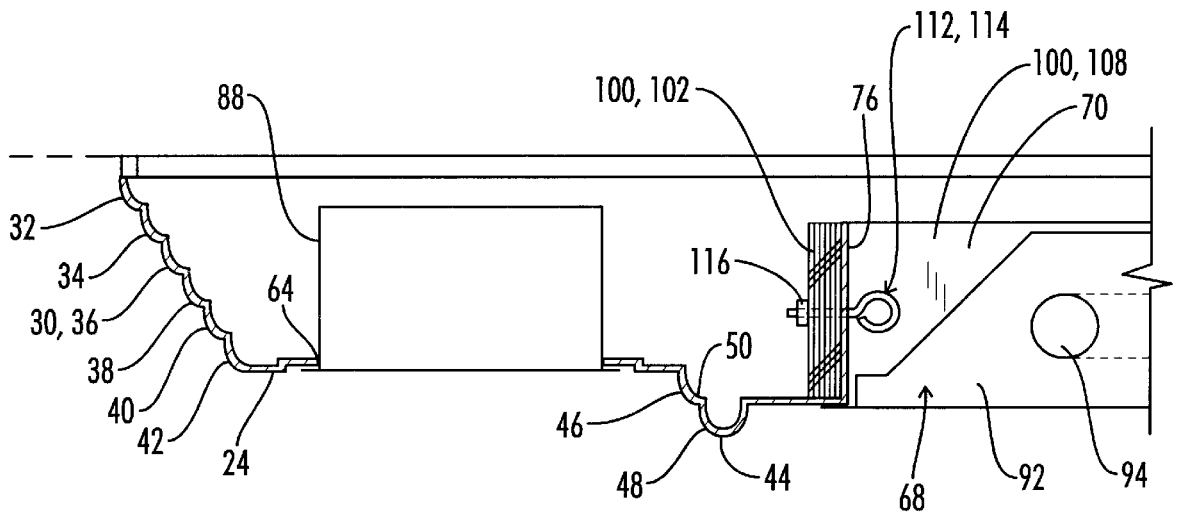
FIG. 5 is an enlarged view of that portion of FIG. 3 shown in the dashed box.
Figure 6:
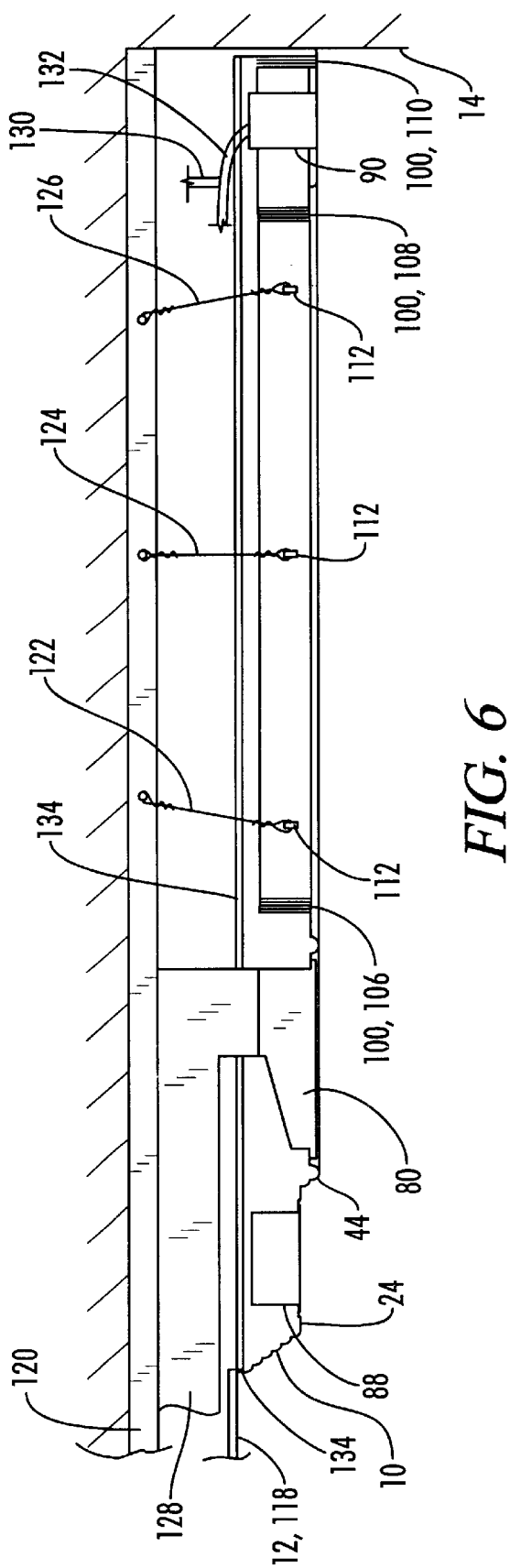
FIG. 6 is a section view taken along line 6—6 of FIG. 2.

The cross-sectional shape of the integrally molded housing 24 is seen in FIGS. 3, 5 and 6. These features are best illustrated in the enlarged view of FIG. 5.

The molded plastic housing 24 includes a sidewall portion 30 which in the bottom view of FIG. 2 can be described as U-shaped or horseshoe shaped.

Figure 4:
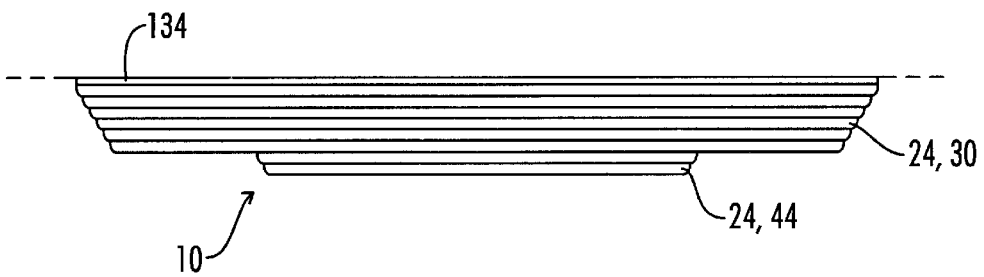
FIG. 4 is an end view of the assembly of FIG. 2 as viewed from the foot of a bed located below the assembly.
Figure 7:
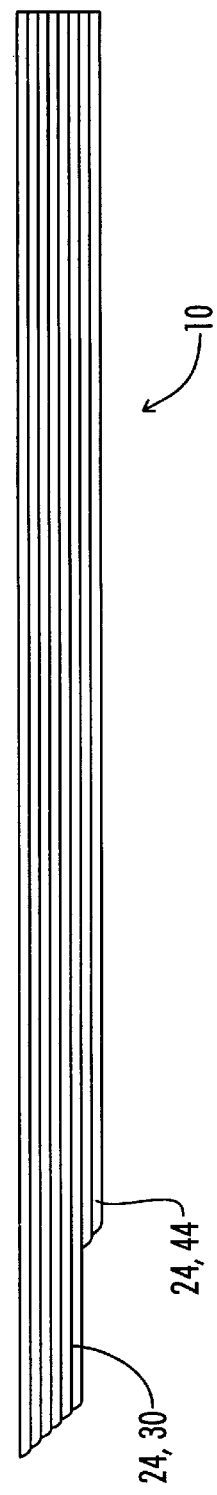
FIG. 7 is a right side view of the assembly of FIG. 2.

As is apparent in the end and side views of FIGS. 4 and 7, respectively, the sidewall portion 30 slopes or tapers inwardly from its outer perimeter toward the central portion of the housing 24. The sidewall portion 30 is molded to include a series of parallel ridges such as 32, 34, 36, 38, 40 and 42. As is apparent in FIG. 5, each of the ridges is formed in the shape of a quarter round, and can be generally described as a partially tubular ridge. Sidewall portion 30 can be described as having a cross-sectional shape including a plurality of steps.

The molded housing 24 also includes a downward extending molded rib 44. As seen in FIG. 5, the rib 44 in cross-section includes two ridges 46 and 48 and can be described as including a step 50.

The ridges molded into the perimeter wall 30 and the rib 44 are both aesthetically pleasing and they provide structural rigidity to the molded plastic housing 24. It will be appreciated that other shapes of ribs or ridges could be utilized to provide a different look while still providing a similar structural rigidity.

Referring to FIG. 2, it is seen that in bottom view the downwardly extending rib 44 can also be described as U-shaped or horseshoe shaped. The rib 44 can be described as being parallel to and located laterally inward of the perimeter wall 30.

Still with reference to FIG. 2, the housing 24 includes a U-shaped or horseshoe shaped flat interior panel 52 which has a plurality of circular task light receiving openings 54, 56, 58, 60, 62, 64, and 66 defined therethrough. The horseshoe shaped interior panel 52 is located between the perimeter wall 30 and the downward extending rib 44.

As best seen in FIGS. 3 and 5, the housing 24 further includes inward of the rib 44, a rectangular shaped interior opening 68. The rectangular shaped opening 68 is formed by four integral vertically extending flanges or walls 70, 72, 74, and 76.

The housing 24 further includes a semi-circular shaped interior opening 78 defined therein adjacent the curved portion of U-shaped rib 44. A semi-circular shaped air diffuser 80 is received in the opening 78. The air diffuser 80 is an off the shelf prior art item and may, for example, be a louvered metal diffuser such as model SSHA sold by the Carnes Company.

The canopy shell 24 further has defined therein adjacent its straight end 26 three additional circular openings 82, 84 and 86. The circular openings 82, 84 and 86 lie in a flat planar portion 87 of housing 24 adjacent the straight end 26 thereof.

As previously noted, the entire housing shell 24 including the perimeter wall 30, flat interior panel 52, downward extending rib 44, and all of the openings defined therein is preferably an integrally molded unitary plastic unit. The molded plastic structure may, for example, be vacuum formed Kydex brand plastic material having a thickness of approximately 0.187".

The openings 54, 56, 58, 60, 62, 64 and 66 may be generally described as task light openings and preferably each will receive a conventional can type lighting fixture such as 88 therein. The task lights may, for example, be LIGHTOLIER model 1102T26T1 fixtures with model 1128T diffusers.

The circular openings 82 and 86 preferably receive conventional can type reading lights therein. The circular opening 84 preferably receives a conventional can type ambient light 90 therein. The reading lights 82 and 86 and the ambient light 84 may, for example, be LIGHTOLIER model 2004 RRWH fixtures.

As best seen in FIGS. 3 and 5, there is a rectangular shaped light box 92 received within the rectangular shaped opening 68. The light box 92 carries conventional fluorescent lamps 94. The light box may, for example, be a LIGHTOLIER 2×4 XT/XR Series Fluorescent Light Fixture.

A translucent bottom panel 96 covers the light box 92 and preferably has a scenic outdoor picture or the like 98 printed thereon which is backlit by the fluorescent lights 94 to provide a pleasing scene to the patient lying below the apparatus 10.

In FIG. 2, a structural frame 100 for the housing 24 is shown in dashed lines. The structural frame 100 includes two lengthwise parallel wooden members 102 and 104 and three transverse members 106, 108 and 110 joining the longitudinal members 102 and 104. The structural framework 100 is preferably constructed from ¾" thick plywood having a vertical height of 4".

The lengthwise members 102 and 104 in combination with the two transverse members 106 and 108 may be described as a rectangular structural frame surrounding the rectangular shaped interior opening 68. As best shown in FIG. 5, this wooden framework is attached to the plastic housing shell 24 by a plurality of eyebolts such as 112 having a circular eye 114 on one end and being attached with a nut 116 on the other end. As can best be seen in FIG. 2, there are preferably six such bolts uniformly placed with three on either side of the rectangular opening 68.

FIG. 6 illustrates the manner in which the canopy assembly 10 is suspended from the ceiling 12.

As will be understood by those skilled in the art, the ceiling 12 typically includes a layer of false ceiling panels 118 which are suspended in a conventional manner from a structural framework 120. The canopy assembly 10 is preferably suspended from this same structural framework 120 by the use of suspension means such as 122, 124, and 126 connected to the eyebolts 112 and to the structural member 120. The suspension means 122 through 126 may be as simple as a strand of twisted wire, or they may include threaded turnbuckles or other conventional apparatus.

Air conditioning duct work 128 is located above the false ceiling 118 and is connected to the semi-circular diffuser 80 to provide heated and/or cooled air to the diffuser 80. Electrical wiring such as 130 from a source in the ceiling is connected to a wiring harness 132 which is connected to each of the various light fixtures previously described.

The duct 128 is commonly referred to as a heating, ventilating and air conditioning or HVAC duct.

A gasket 134 fits around the upper perimeter edge of the molded housing 24 to provide a seal between the housing 24 and the false ceiling 118. The gasket 134 is preferably a ½" square black foam gasket.

Thus, the structural framework 100 is attached to and supported from the ceiling structure 120, and the molded housing 24 is attached to and supported from the framework 100, so that the canopy assembly 10 is supported from the ceiling structure 120.

Thus, it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A canopy assembly for mounting on a ceiling over a bed, comprising:
    an elongated housing having a straight first end for abutting a wall adjacent a head of the bed, and having a rounded second end, the housing including:
        a horseshoe shaped interior panel having a plurality of light receiving openings defined therein;
        a rectangular shaped interior opening; and
        a semi-circular shaped interior opening;
    a semi-circular shaped air diffuser disposed in the semi-circular shaped interior opening;
    a rectangular light box disposed in the rectangular shaped interior opening; and
    a plurality of light fixtures, one of which is received in each of the light receiving openings of the horseshoe shaped interior panel.

2. The canopy assembly of claim 1, wherein:
    the housing comprises an integrally molded plastic shell.

3. The canopy assembly of claim 2, wherein:
    the housing includes a horseshoe shaped sidewall portion shaped in cross-section as a series of parallel partially tubular ridges.

4. The canopy assembly of claim 3, wherein:

the sidewall assembly is sloped inwardly from an outer perimeter of the sidewall assembly to the horseshoe shaped interior panel.

5. The canopy assembly of claim 1, wherein:

the housing includes a flat planar portion adjacent the straight first end of the housing; and the assembly further includes:

a reading light mounted on the flat planar portion; and an ambient light mounted on the flat planar portion.

6. The canopy assembly of claim 1, further comprising:

a rectangular structural frame surrounding the rectangular shaped interior opening, the frame being attached to the housing so that the housing is supported from the frame.

7. The canopy assembly of claim 6, further comprising:

means for suspending the frame from the ceiling over the bed.

8. The canopy assembly of claim 1, further comprising:

a gasket for sealing between the housing and the ceiling.

9. The canopy assembly of claim 1, further comprising:

a translucent scenic panel disposed in the rectangular light box.

10. The canopy assembly of claim 1, further comprising:

an HVAC duct connected to the air diffuser.

11. A lighting and ventilation apparatus for use over a bed in a health care facility, comprising:

the a unitary molded plastic housing elongated in shape to overlie the bed, the housing having defined therein:

a first task light opening;

a air diffuser opening;

a light box opening; and an air supply diffuser disposed in the diffuser opening.

12. The apparatus of claim 11, wherein:

the housing includes an interior portion and a perimeter portion;

the diffuser opening and light box opening are located in the interior portion of the housing; and the apparatus includes a plurality of task light openings including the first task light opening, and the task light openings are located in the perimeter portion.

13. The apparatus of claim 11, wherein the housing further includes defined therein:

an ambient light opening; and a reading light opening.

14. The apparatus of claim 11, further comprising:

a structural framework attached to the housing so that the housing is supported from the framework.

15. The apparatus of claim 11, wherein:

the housing includes an inwardly tapered perimeter wall around at least a portion thereof, the perimeter wall including a plurality of parallel integrally molded horizontal ridges.

16. The apparatus of claim 15, wherein:

the light box opening is rectangular;

the diffuser opening is semi-circular and is located adjacent an end of the light box opening; and the housing includes a plurality of task light openings arranged in a horseshoe shaped pattern around the light box opening and the diffuser opening.

17. The apparatus of claim 11, wherein:

the housing includes an upwardly extending rectangular wall defining the light box opening.

18. The apparatus of claim 17, wherein:

the housing includes a horseshoe shape downward extending molded rib located such that the diffuser opening and the light box opening are contained within the horseshoe shape and the task light opening is outside the horseshoe shape.

19. The apparatus of claim 18, wherein:

the rib has a cross-sectional shape including a step.

20. A canopy assembly mounted on a ceiling of a room over a bed, comprising:

a structural framework supported from the ceiling;

a housing attached to and supported from the structural framework;

an air diffuser mounted in the housing above a foot of the bed;

a light box including a back-lighted translucent scenic panel mounted in the housing above the bed; and a plurality of task lights mounted in the housing on opposite sides of the light box.

21. The canopy assembly of claim 20, wherein:

the housing includes a molded plastic shell having an inwardly downwardly tapered perimeter wall including a plurality of parallel integrally molded horizontal ridges.

22. The canopy assembly of claim 21, wherein:

the housing includes a horseshoe shaped downwardly extending molded rib, the downwardly extending rib being parallel to and located laterally inward of the perimeter wall.

23. The canopy assembly of claim 22, wherein:

the task lights are located between the perimeter wall and the rib.

24. A method of providing light and air conditioning to a space above a bed, comprising:

attaching a molded housing to a structural framework, the housing including an air diffuser and a light;

attaching the framework to a ceiling structure so that the framework and housing are supported from the ceiling and so that the molded housing abuts the ceiling;

connecting an air conditioning supply duct from within the ceiling to the air diffuser; and connecting electrical wiring from within the ceiling to the light.

* * * * *